US006328949B1

(12) United States Patent
Tessarolo et al.

(10) Patent No.: US 6,328,949 B1
(45) Date of Patent: Dec. 11, 2001

(54) NAIL COVERING SYSTEM

(76) Inventors: Dino Tessarolo; Anna Tessarolo, both of 866 Main St. East, Hamilton ON (CA), L8M 1L9

( * ) Notice: Subject to any disclaimer, the term of this patent is extended or adjusted under 35 U.S.C. 154(b) by 0 days.

(21) Appl. No.: 09/413,018

(22) Filed: Oct. 6, 1999

Related U.S. Application Data

(60) Provisional application No. 60/104,206, filed on Oct. 14, 1998.

(51) Int. Cl.[7] .............................. A61K 7/04; A45D 29/00
(52) U.S. Cl. ................................ 424/61; 132/73; 434/100
(58) Field of Search ............................... 434/100; 132/73; 118/406; 424/61

(56) References Cited

U.S. PATENT DOCUMENTS 4,600,030 7/1986 Newman ............................. 132/88.5
4,767,648 8/1988 Hokama et al. ....................... 428/15
4,974,610 * 12/1990 Orsini ..................................... 132/73
5,044,384 9/1991 Hokama et al. ..................... 132/200
5,309,365 * 5/1994 Sullivan et al. ................ 364/474.03
5,873,375 * 2/1999 Johnson et al. ...................... 132/200
6,035,860 * 3/2000 Mombourquette ................... 132/200
6,065,969 * 5/2000 Rifkin et al. ......................... 434/100
6,067,996 * 5/2000 Weber et al. .......................... 132/73

* cited by examiner

*Primary Examiner*—Thurman K. Page
*Assistant Examiner*—S. Howard

(57) ABSTRACT

The present invention a method for making nail coverings comprises the steps of scanning a persons fingernail to produce a digitized nail image of the nail top surface and shaping a nail covering material using the digitized nail image such that the nail covering material conforms to the nail top surface thereby producing a nail cover sized to cover substantially the entire nail top surface. The invention preferably includes the step of adhering the nail cover to the nail top surface thereby covering substantially the entire nail top surface with the nail cover. The invention preferably includes the further step of producing a three dimensional digital nail image of the nail top surface.

17 Claims, 5 Drawing Sheets

NAIL COVERING SYSTEM

This application claims benefit of provisional application No. 60/104,206, filed Oct. 14, 1998.

FIELD OF THE INVENTION

The present invention relates generally to finger nail covering and finishing and more particularly to a new finger nail covering system.

BACKGROUND OF THE INVENTION

Presently finger nails are finished using liquid nail polishes which are applied manually using brushes and/or are sprayed onto the finger nails using air brushing. The liquid nail polish is applied to the finger nail and a substantial drying period is required before the finger nails are in a usable state. In addition to coloured nail polishes, often clear polishes are applied over top of the coloured polishes in order to provide for increased durability of the nail polish and as well for increased gloss and look of the nail polish. The clear covering is also applied by either using a brush or spraying with an air brush. A substantial drying period is required before the nails are in a usable state.

Over time the nail polish applied by the liquid means begins to wear either through use of the nails which creates chipping and/or wearing off of the colouring over time and/or the nails grow out to the point where there is a substantial portion of the nail nearest the nail bed were there is no nail polish covering where the new nail has grown out. Once any of the above has occurred, the nail polish must be removed, normally using very strong solvents, and again, a substantial amount of time and effort is required in order to remove the existing nail polishes from the finger nails.

The presently accepted method of nail polishing requires a considerable amount of time, effort and skill on the part of the person applying the nail polish and again on the part of the person who is removing the nail polish from the fingers.

There are a number of inventions that have tried to address the problems of time and skill required to apply conventional nail polishes in for example, U.S. Pat. No. 4,974,876 by Larson issued Aug. 14, 1990, U.S. Pat. No. 4,974,610 by Orsini issued Dec. 4, 1990, U.S. Pat. No. 4,600,030 by Newman issued Jul. 15, 1986, U.S. Pat. No. 5,525,389 by Hans-Rainer Hoffman issued Jun. 11, 1996, U.S. Pat. No. 3,898,357 by Albert C. Miller issued Aug. 5, 1975, U.S. Pat. No. 5,415,903 by Hans-Rainer Hoffman issued May 16, 1995 as well as U.S. Pat. No. 5,903,840 by Dae S. So issued Feb. 27, 1990.

While the above-mentioned patented inventions may be suitable for the particular purpose to which they address, they would not be suitable for the purpose of the present invention as hereafter described. In particular there is a need for a fast, durable, easy to apply and remove nail covering which is inexpensive and easily accessible by those wanting to finish their nails in any particular fashion.

SUMMARY OF THE INVENTION

The present invention; a method for making nail coverings comprises the steps of:

(a) scanning a persons fingernail to produce a digitized nail image of the nail top surface; and (b) shaping nail covering material using the digitized nail image such that the nail covering material conforms to the nail top surface thereby producing a nail cover sized to cover substantially the entire nail top surface.

Preferably including a further step of adhering the nail cover to the nail top surface thereby covering substantially the entire nail top surface with the nail cover.

Preferably the step of scanning includes producing a three dimensional digital nail image of the nail top surface.

Preferably the step of scanning includes producing a two dimensional digital nail image of the nail top surface.

Preferably including a further step of adjusting the dimension of the two dimensional image to correct for the curvature of the actual nail top surface.

Preferably the nail covering material includes a thin film type material.

Preferably the nail covering material includes a self adhesive thin film type material.

Preferably the step of shaping includes using a plotter to cut nail covering material using the digitized nail image such that the nail covering material conforms to the nail top surface thereby producing a nail cover sized to cover substantially the entire nail top surface.

Preferably including a further step of scanning a transverse nail section in order to adjust the size of the two dimensional image to correct for the curvature of the actual nail top surface.

The present invention a apparatus for making nail coverings comprises:

(a) a scanning means for scanning a persons fingernail to produce a digitized nail image of the nail top surface; and (b) a computer controlled shaping means for shaping nail covering material using the digitized nail image such that the nail covering material conforms to the nail top surface thereby producing a nail cover sized to cover substantially the entire nail top surface.

Preferably further comprising an adjusting means for adjusting the size of the two dimensional digital image to correct for the curvature and size of the actual nail top surface.

Preferably further comprising an adhering means for adhering the nail cover to the nail top surface thereby covering substantially the entire nail top surface with the nail cover.

Preferably said scanning means is adapted to produce a three dimensional digital nail image of the nail top surface.

Preferably said scanning means is adapted to produce a two dimensional digital nail image of the nail top surface.

Preferably said scanning means is further adapted to adjust the dimension of the two dimensional digital image to correct for the curvature of the actual nail top surface.

Preferably said shaping means includes a computer controlled plotter capable of cutting nail covering material utilizing the digitized nail image such that the nail covering material conforms to the nail top surface, thereby producing a nail cover size to cover substantially the entire nail top surface.

Preferably said scanning means is further adapted to scan a transverse nail section which is used to adjust the size of the two dimensional image to correct for the curvature of the actual nail top surface.

Preferably the nail covering material preferably includes a thin film type material.

Preferably said self adhesive thin film type material is preferably a thin vinyl sheet having a self adhesive backing which is capable of adhering to the nail top surface.

A presently preferred embodiment of the present invention a method for making nail coverings comprises the steps of:

(a) scanning a persons fingernail to produce a two dimensional digitized nail image of the nail top surface.

(b) adjusting the size of the two dimensional image to correct for the curvature and size of the actual nail top surface.

(c) shaping nail covering material to conform to the nail image created to produce a nail cover sized to cover substantially the entire nail top surface.

(d) adhering the nail cover to the nail thereby covering substantially the entire nail top surface with the nail cover.

BRIEF DESCRIPTION OF THE DRAWINGS

The invention will now be described by way of example only, with references to the following drawings in which.

DETAILED DESCRIPTION OF THE PREFERRED EMBODIMENTS

Definitions

Figure 1:
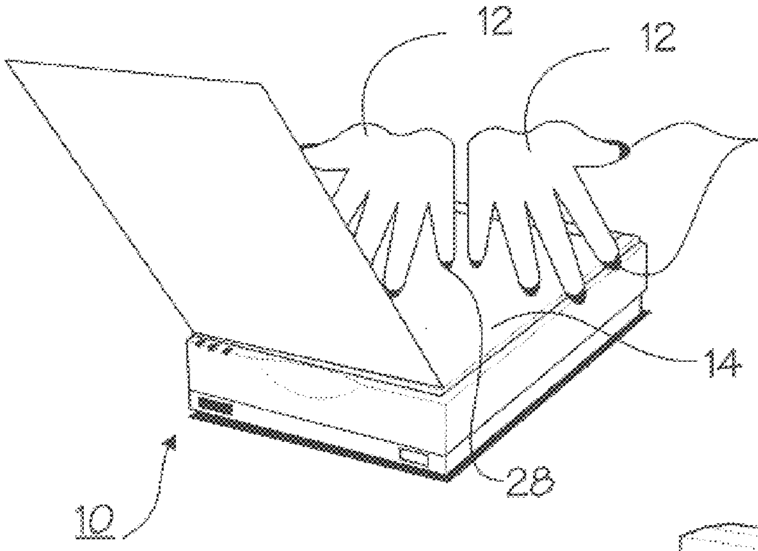
FIG. 1 is a schematic representation of a pair of hands being applied to a scanner illustrating how finger nails can be scanned into a scanning device.
Figure 2:
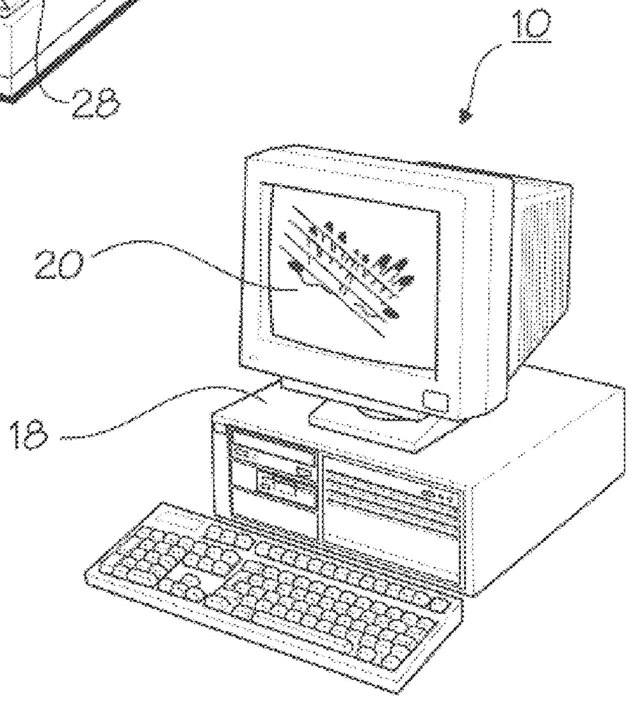
FIG. 2 shows schematically how the digitized nail images appear on a computer screen and can be imported from the scanner to a computer.
Figure 3:
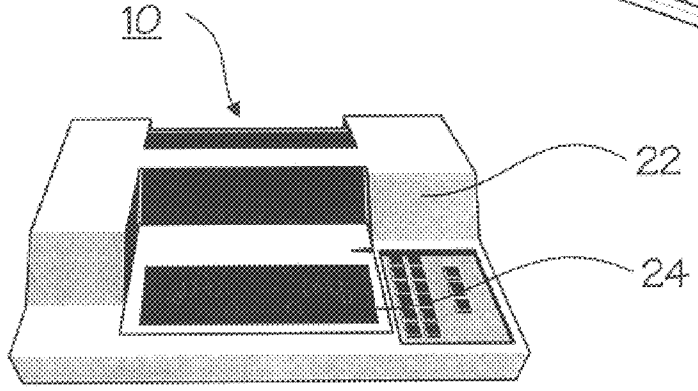
FIG. 3 is a schematic showing a plotter cutting nail covers out of self adhesive vinyl.

Thin Film Type Material: material which is suitable for application to a fingernail which typically is not thicker than the thickness of a fingernail.

Plotter: a computer plotter which is capable of drawing or cutting replica's of digital images stored within the computer onto paper or thin film type materials. Also known as laser plotters, pen plotters, knife plotters etc.

Scan or Scanning: refers to any method known in the art for digitizing objects including but not limited to probe scanners, touch scanners, flatbed laster scanners, etc.

In the present invention, FIGS. 1 through 6 schematically depict the apparatus and the steps required in order to carry out the present nail covering system shown generally as 10. Hands 12 are placed palm up onto scanner 14 such that finger nails 16 are oriented as parallel as possible to the scanning surface 28. If need be an additional scan is done for the thumb nails in order that as accurate an image of finger or thumb nail 16 is scanned into computer 18 shown in FIG. 2.

Figure 9:
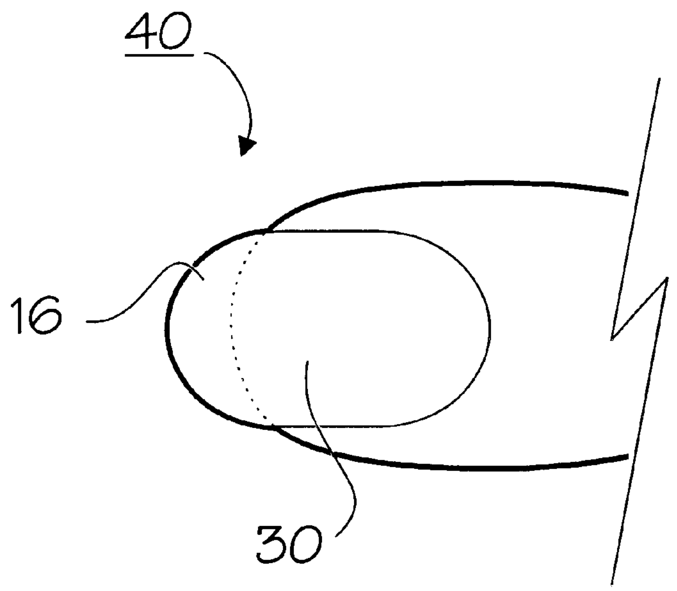
FIG. 9 is a top plan view of the tip of finger showing the finger nail as well as the nail top surface.
Figure 10:
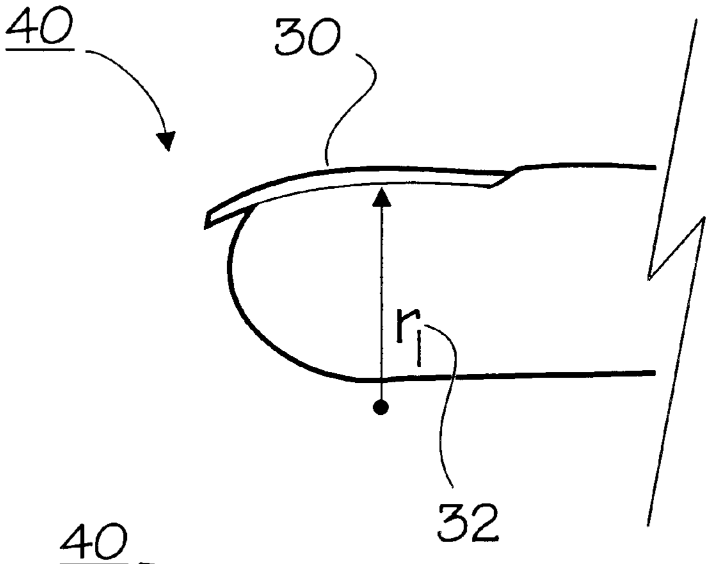
FIG. 10 is a side elevational cross sectional view schematically depicting the longitudinal nail curvature and the finger nail.
Figure 11:
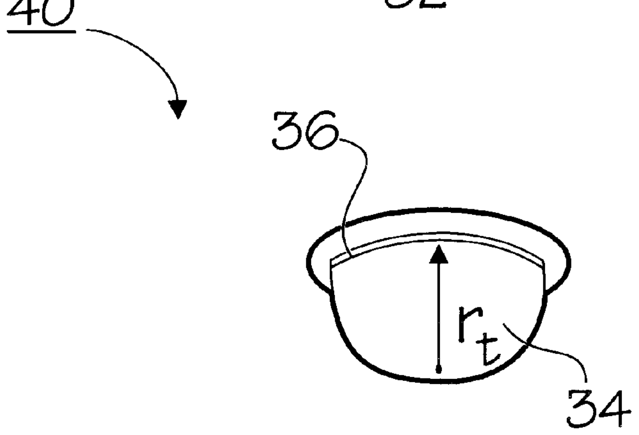
FIG. 11 is a transverse cross sectional elevational view showing the transverse nail curvature and the frontal portion of a finger and finger nail tip.

Scanning a persons finger nails, produces a digitized nail image 20 of the nail top surface 30 which can be displayed by compute 18 and which can be imported into a graphics program such as Corel Draw® for further processing. Referring now additionally to FIGS. 9, 10 and 11 depicting schematically a finger tip 40 showing a finger nail 16 having a nail top surface 30, a longitudinal nail curvature 32 as well as a transverse nail curvature 34 and a transverse nail section 36.

The present invention contemplates the possibility of scanning into computer a three dimensional digitized image of the nail top surface 30. In practice, however, it is found to be more practical to scan into the computer a two dimensional digital image 20 of the nail top surface 30 for cost and time savings reasons. Unfortunately a finger nail 16 as depicted in 9, 10 and 11 generally speaking is not flat and therefore a two dimensional image is an approximation of the three dimensional surface of the nail top surface 30. Strictly speaking the curvature of the nail top surface 30 includes the longitudinal nail curvature 32 as well as the transverse nail curvature 34. These curvatures should be taken into account and the two dimensional digitized nail image 20 normally is adjusted in order to ensure that the two dimensional digitized nail image 20 corresponds substantially with the three dimensional nail top surface 30.

In practice digitized nail image 20 can be adjusted manually by trial and error, such that the digitized nail image 20 corresponds substantially to the nail top surface 30. The digitized nail image 20 can also be adjusted through using standardized values for transverse nail curvature 34 as well as longitudinal nail curvature 32 in order to automatically adjust the digitized nail image 20 once it is imported into computer 18. Finally, it is possible to more accurately adjust digitized mail image 20 by applying mathematical formulae and measuring the transverse nail curvature 34 by scanning transverse nail section 36 into scanner 28, thereby obtaining an actual transverse nail curvature 34 for each nail and then correcting the digitized nail image 20 with the information obtained from the transverse nail curvature 34. Note that the major curvature of finger nail 16 is the transverse nail curvature 34 rather than the longitudinal nail curvature 32 and therefore, the correction for the transverse nail curvature 34 is more critical than the longitudinal nail curvature 32.

Figure 4:
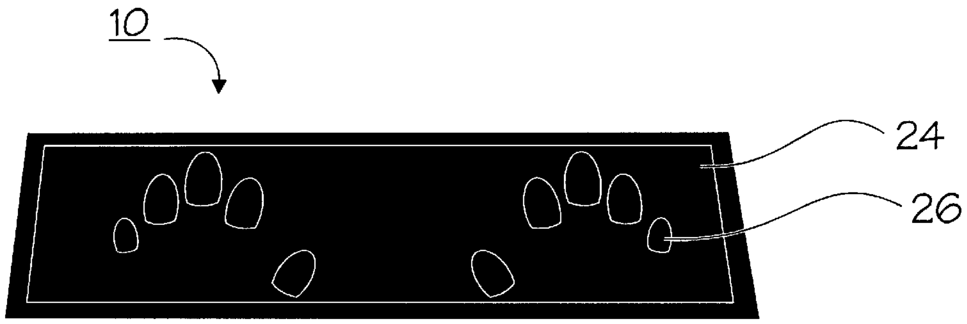
FIG. 4 shows the self adhesive vinyl with the nail covers in situ cut into their final shape.
Figure 5:
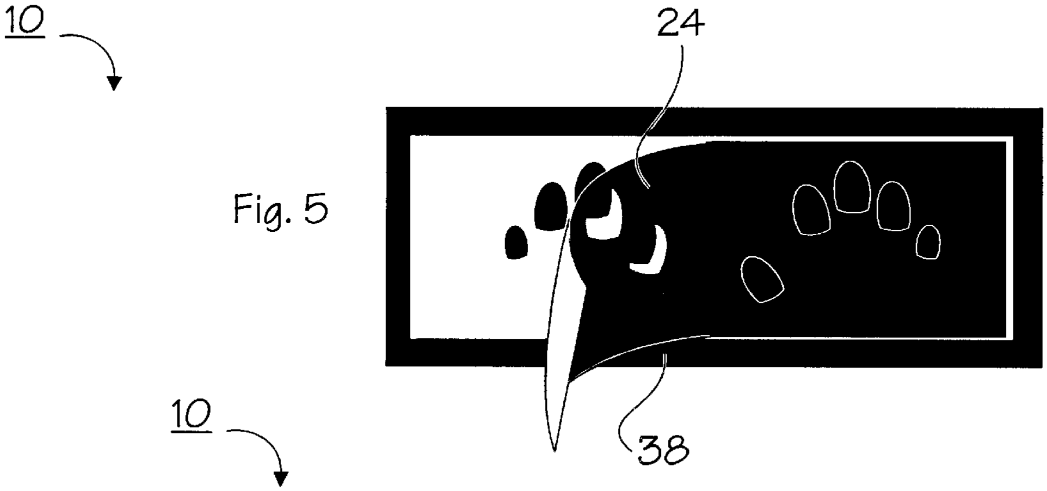
FIG. 5 schematically depicts excess vinyl being peeled from the backing leaving in place the nail covers on the self adhesive vinyl backing.
Figure 6:
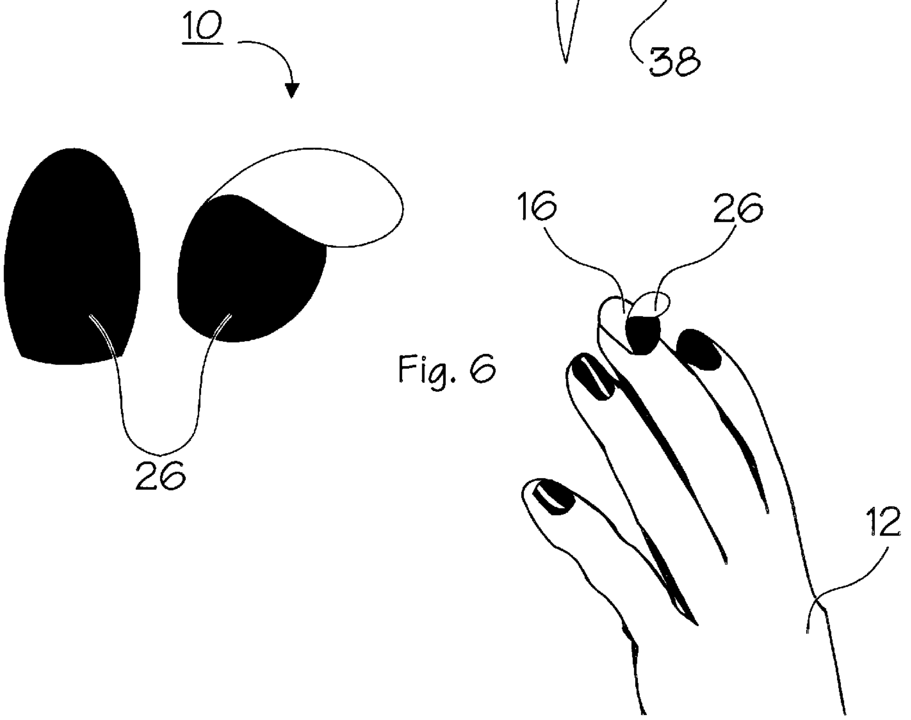
FIG. 6 schematically depicts a nail cover being applied to a finger nail.

Referring now again to FIGS. 1 through 6, once digitized nail image 20 is in computer 18 it can be imported into a graphics program such as Corel Draw® 7 and corrected for size as described above and then saved onto disc for future customer reference. Digitized nail image 20 can then be communicated to a plotter 22 which is fed with a self adhesive vinyl 24. Plotter 22 is capable of cutting nail covers 26 out of the self adhesive vinyl 24 which correspond in size and shape to the digitized nail image 20. The self adhesive vinyl 24 is removed from plotter 22. FIG. 4 schematically depicts the nail covers 26 for each finger and thumb of a particular persons hand 12. The customer simply peels back excess vinyl 38 from self adhesive vinyl 24 leaving nail cover 26 on self adhesive vinyl 24. The nail covers 26 are then easily removed from self adhesive vinyl 24 and carefully placed onto finger nails 16 of hand 12 thereby creating an instant nail finish which covers substantially the entire nail top surface 30 of finger nail 16.

The method of the present nail covering system can be summarized as follows:

1. Scanning a persons finger nail 16 to produce a digitized nail image 20 of the nail top surface 30.
2. Shaping and/or cutting the nail covering material which preferably is self-adhesive vinyl 24 using the digitized nail image 20 in order to produce a nail cover to conform to the nail top surface 30 which is sized to cover substantially the entire nail top surface 30.
3. Adhering the nail cover 26 so produced, preferably by peeling a nail cover 26 from self adhesive vinyl 24 and carefully placing these onto the nail top surface 30 of finger nail 16 thereby covering substantially the entire nail top surface 30 with nail covers 26.

Figure 7:
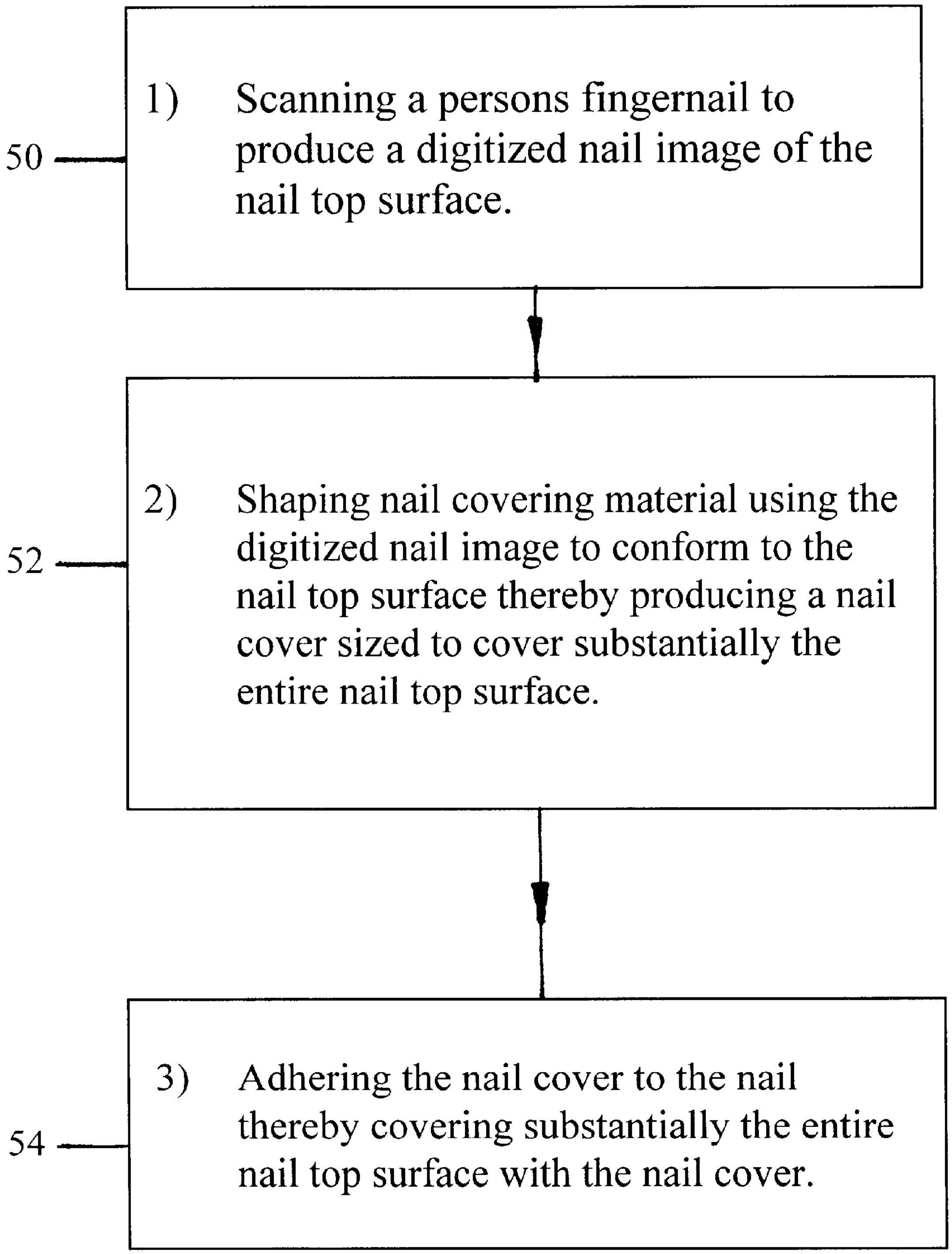
FIG. 7 is a flow chart indicating the preferred method of using the nail covering system.

These steps are depicted in flow chart form in FIG. 7 as steps 50, 52 and 54 respectively.

In a presently preferred embodiment, the method of using the nail covering system is as follows:

1. Scanning a persons finger nail 16 to produce a two dimensional digitized nail image 20 of a persons nail top surface 30.
2. Adjusting the size of the two dimensional digitized nail image 20 to correct for the curvature and size of the nail top surface 30.
3. Shaping and/or cutting the nail covering material which preferably is self-adhesive vinyl 24 using the digitized nail image 20 in order to produce a nail cover to conform to the nail top surface 30 which is sized to cover substantially the entire nail top surface 30.
4. Adhering the nail cover 26 so produced, preferably by peeling a nail cover 26 from self adhesive vinyl 24 and carefully placing these onto the nail top surface 30 of finger nail 16 thereby covering substantially the entire nail top surface 30 with nail covers 26.

Figure 8:
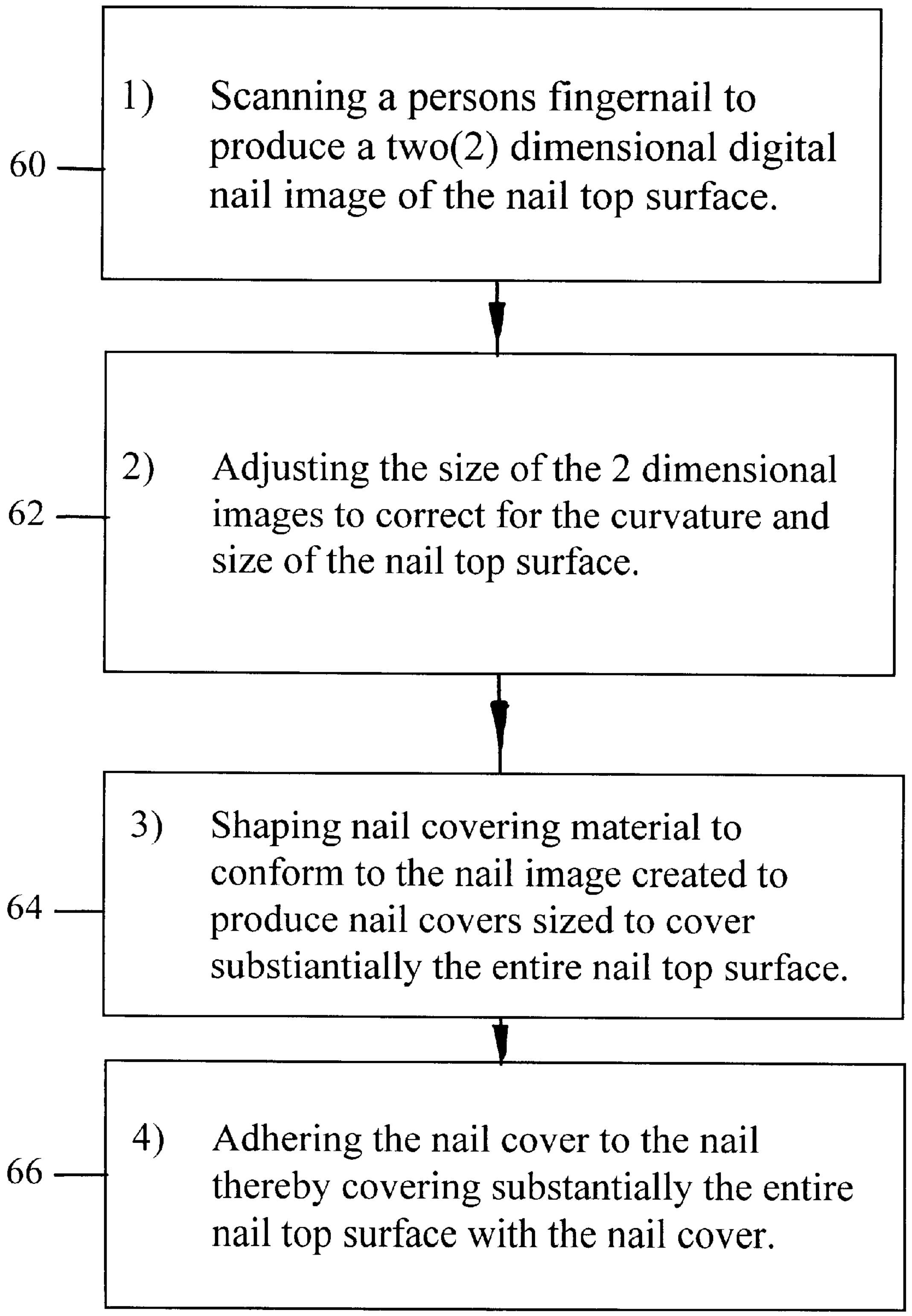
FIG. 8 is a flow chart showing another preferred embodiment and method for using the nail covering system.

These steps are depicted in flow chart form in FIG. 8 as steps 60, 62, 64 and 66 respectively.

It will be apparent to those skilled in the art that the nail covering material which preferably is self adhesive vinyl 24 can be many different types of materials. The present invention contemplates that material without a self adhesive backing can also be used. In this case an additional glue and or step of applying a glue to the nail and/or the nail cover 26 would have to be included.

It will also be apparent to those skilled in the art that various colours, designs, shapes and many other graphics can be applied to nail cover 26. Without limiting the generality of the possibilities of the designs of nail covers 26 they can be solid colours, graphic designs, printed designs and/or many other graphic and printed designs can be applied to nail covers 26, before and/or after applying the nail cover 26 to finger nail 16.

It should accordingly, be apparent to persons skilled in the art that various modifications and adaptations of the structure described above are possible without departure from the spirit of the inventions, the scope of which is defined in the appended claims.

We claim:

1. A method for making nail coverings comprising the steps of:

(a) scanning a persons fingernail to produce a digitized nail image of the nail top surface; and (b) shaping nail covering material using the digitized nail image such that the nail covering material conforms to the nail top surface thereby producing a nail cover sized to cover substantially the entire nail top surface; and (c) comprising a further step of adhering the nail cover to the nail top surface thereby covering substantially the entire nail surface with the nail cover.

2. The method of claim 1 wherein the step of scanning includes producing a three dimensional digital nail image of the nail top surface.

3. The method of claim 1, wherein the step of scanning includes producing a two dimensional digital nail image of the nail top surface.

4. The method of claim 3, including a further step of adjusting the dimension of the two dimensional image to correct for the curvature of the actual nail top surface.

5. The method of claim 1 wherein the nail covering material includes a thin film material.

6. The method of claim 1, wherein the nail covering material includes a self adhesive thin film material.

7. The method of claim 1, wherein the step of shaping includes using a plotter to cut nail covering material using the digitized nail image such that the nail covering material conforms to the nail top surface thereby producing a nail cover sized to cover substantially the entire nail top surface.

8. The method of claim 4, comprising a further step of scanning a transverse nail section in order to adjust the size of the two dimensional image to correct for the curvature of the actual nail top surface.

9. Apparatus for making nail coverings comprising:

(a) a scanning means for scanning a persons fingernail to produce a digitized nail image of the nail top surface; and (b) a computer controlled shaping means for shaping nail covering material using the digitized nail image such that the nail covering material conforms to the nail top surface thereby producing a nail cover sized to cover substantially the entire nail top surface;

(c) further comprising an adjusting means for adjusting the size of the two dimensional digital image to correct for the curvature and size of the actual nail top surface, and (d) further comprising an adhering means for adhering the nail cover to the nail top surface thereby covering substantially the entire nail top surface with the nail cover.

10. The apparatus for making nail coverings claimed in claim 9 wherein said scanning means is adapted to produce a three dimensional digital nail image of the nail top surface.

11. The apparatus for making nail coverings claimed in claim 9 wherein said scanning means is adapted to produce a two dimensional digital nail image of the nail top surface.

12. The apparatus for making nail coverings claimed in claim 11 wherein said scanning means is further adapted to adjust the dimension of the two dimensional digital image to correct for the curvature of the actual nail top surface.

13. The apparatus for making nail coverings claimed in claim 12 wherein said shaping means includes a computer controlled plotter capable of cutting nail covering material utilizing the digitized nail image such that the nail covering material conforms to the nail top surface, thereby producing a nail cover size to cover substantially the entire nail top surface.

14. The apparatus for making nail coverings claimed in claim 12 wherein said scanning means is further adapted to scan a transverse nail section which is used to adjust the size of the two dimensional image to correct for the curvature of the actual nail top surface.

15. The apparatus for making nail coverings claimed in claim 14 wherein the nail covering material preferably includes a thin film material.

16. The apparatus for making nail coverings claimed in claim 15 wherein said self adhesive thin film material is preferably a thin vinyl sheet having a self adhesive backing which is capable of adhering to the nail top surface.

17. A method for making nail coverings comprising the steps of:

(a) scanning a persons fingernail to produce a two dimensional digitized nail image of the nail top surface.

(b) adjusting the size of the two dimensional image to correct for the curvature and size of the actual nail top surface.

(c) shaping nail covering material to conform to the nail image created to produce a nail cover sized to cover substantially the entire nail top surface.

(d) adhering the nail cover to the nail thereby covering substantially the entire nail top surface with the nail cover.

* * * * *